(12) United States Patent
Hensley et al.

(10) Patent No.: US 8,916,211 B2
(45) Date of Patent: Dec. 23, 2014

(54) METHOD AND COMPOSITION FOR PREVENTING AND TREATING AVIAN INFLUENZA IN POULTRY

(71) Applicant: Abattis Bioceuticals Corp., Vancouver (CA)

(72) Inventors: Charles Hensley, Cypress, CA (US); Sung Pyo, Irvine, CA (US)

(73) Assignee: Abattis Bioceuticals Corp., Vancouver BC (CA)

( * ) Notice: Subject to any disclaimer, the term of this patent is extended or adjusted under 35 U.S.C. 154(b) by 0 days.

(21) Appl. No.: 13/900,235

(22) Filed: May 22, 2013

(65) Prior Publication Data

US 2013/0253047 A1    Sep. 26, 2013

Related U.S. Application Data

(63) Continuation of application No. 11/903,517, filed on Sep. 20, 2007, now abandoned.

(60) Provisional application No. 60/846,311, filed on Sep. 20, 2006.

(51) Int. Cl.
| | |
|---|---|
| *A61K 36/82* | (2006.01) |
| *A61K 39/21* | (2006.01) |
| *A61K 45/06* | (2006.01) |
| *A61K 31/352* | (2006.01) |
| *A61K 31/353* | (2006.01) |

(52) U.S. Cl.
CPC ............. *A61K 31/352* (2013.01); *A61K 45/06* (2013.01); *A61K 31/353* (2013.01); *A61K 36/82* (2013.01)
USPC ........................................ 424/729; 424/207.1

(58) Field of Classification Search
CPC ............ A61K 2300/00; A61K 31/535; A61K 31/7024; A61K 45/06
USPC ........................... 424/729, 204, 206, 209, 725
See application file for complete search history.

(56) References Cited

U.S. PATENT DOCUMENTS

| 6,428,818 B1 | 8/2002 | Morré et al. |
| 2004/0097430 A1 | 5/2004 | Zhao et al. |

FOREIGN PATENT DOCUMENTS

| EP | 0417385 A2 | 3/1991 |
| JP | 08053353 | 2/1996 |
| JP | 10075718 | 3/1998 |
| JP | 10075718 A * | 3/1998 |

OTHER PUBLICATIONS

Guralnik et al., "Limitations of Current Prophylaxis Against Influenza Virus Infection", American Journal of Therapeutics, vol. 14, Issue 5, pp. 449-454, Sep./Oct. 2007.
Joslyn et al., "Comparitive Effects of Gallotannic Acid and Related Phenolics on the Growth of Rats", Journal of Nutrition, Issue 98, pp. 119-126, 1969.
Kramesonline, "Avian Influenza A (H5N1) Virus Vaccine", http://wishard.kramesonline.com/Medications/26.3561, Apr. 20, 2009.
Leung et al., "Theaflavins in Black Tea and Catechins in Green Tea Are Equally Effective Antioxidants", Journal of Nutrition, Issue 131, Biochemical and Molecular Action of Nutrients Research Communication, American Society for Nutritional Sciences, pp. 2248-2251, 2001.
Mohammad Najmul Ghani Khan, Khazaain-al-Advia, vol. II (20$^{th}$ Century AD), Nadeem Yunus Printer/Sheikh Mohd Basheer & Sons, Lahore, 1911 AD, p. 342-343, Formulation Id: AN2/324, Formulation Name: Chai.
Mohammad Najmul Ghani Khan, Qaraabaadeen Najm-al-Ghani (20$^{th}$ Century AD), Munshi Nawal Kishore Lucknow, (Second Edition), 1928 AD, p. 202, Formulation Id: NA4/1220A, Formulation Name: Dawa-e-nazla.
Mohammad Najmul Ghani Khan, Qaraabaadeen Najm-al-Ghani (20$^{th}$ Century AD), Munshi Nawal Kishore Lucknow, (Second Edition), 1928 AD, p. 594, Formulation Id: NA4/3925, Formulation Name: Hab-e-chai Deegar Qawi Tar.
Mohammad Najmul Ghani Khan, Khazaain-al-Advia, vol. II (20$^{th}$ Century AD), Nadeem Yunus Printer/Sheikh Mohd Basheer & Sons, Lahore, 1911 AD, p. 657, Formulation Id: AN2/661N, Formulation Name: Joshaanda-e- Roosa Barae Humma.
Mohammad Najmul Ghani Khan, Khazaain-al-Advia, vol. II (20$^{th}$ Century AD), Nadeem Yunus Printer/Sheikh Mohd Basheer & Sons, Lahore, 1911 AD, p. 343, Formulation Id: AN2/324I, Formulation Name: Matbookh Barae Nazla Wa Zukaam.
Mohammad Najmul Ghani Khan, Qaraabaadeen Najm-al-Ghani (20$^{th}$ Century AD), Munshi Nawal Kishore Lucknow, (Second Edition), 1928 AD, p. 549, Formulation Id: NA4/3621, Formulation Name: Qahwa-e-chai.
PA Pandemic Influenza Preparedness Planning Summit, "Influenza Virus Types, Subtypes, and Strains", 2006.
Planet Tea, "Preparing Green Tea, White Tea, Black and Oolong Tea, Herbal and Chai Tea," http://www.planet-tea.com/preparation.html, pp. 1-2, Aug. 9, 2012.
Song et al., "Antiviral Effect of Catechins in Green Tea on Influenza Virus", Anitiviral Research, Issue 68, pp. 66-74, 2005.

* cited by examiner

*Primary Examiner* — Chris R Tate
*Assistant Examiner* — Deborah Davis
(74) *Attorney, Agent, or Firm* — Dunlap Codding P.C.

(57) ABSTRACT

A method and composition for preventing and treating avian influenza utilizes an effective quantity of polyphenolic(s) and its derivatives in combination with a carrier. The anti-avian influenza ingredient having a composition selected from the group consisting of theaflavin, theaflavin-3,3'-digallate, theaflavin-3-monogallate, theaflavin-3 gallate, theaflavin-3'-gallate, thearubigin, gallic acid, tannic acid, (−)-epigallocatechin gallate (EGCG), (−)epigallocatechin (EGC), (+)-epicatechin (EC), (−)-gallocatechin gallate (GCG), and catechin.

18 Claims, No Drawings

METHOD AND COMPOSITION FOR PREVENTING AND TREATING AVIAN INFLUENZA IN POULTRY

RELATED APPLICATIONS

This application is a continuation of U.S. application Ser. No. 11/903,517 filed Sep. 20, 2007, which claims the benefit of U.S. Provisional Application Ser. No. 60/846,311, filed on Sep. 20, 2006, the entire contents of both of which are herein incorporated by reference in their entirety.

BACKGROUND OF THE PRESENT INVENTION

1. Field of Invention

This invention relates to methods and compositions for preventing and treating disease in poultry.

2. Description of Related Arts

Poultry are domesticated birds that are raised by farmers for meat and eggs. Poultry includes, without limitation, chickens, ducks, geese, turkeys, guinea fowl, and pheasants. An example of a commercially raised duck is the White Pekin duck.

Examples of commercially raised geese are Embden, Toulouse, Chinese goose, African goose, Sebastopol, Pilgrim, and American Buff breeds. Examples of commercially raised turkeys include White, Hollands, Bronze, Narragansett, Bourbon Red, Black, Slate, Royal Palm, Beltsville, and Small White breeds.

Examples of commercially raised chickens include the American Class, the Asiatic Class, the English Class, and the Mediterranean Class. The American Class includes Buckeye, Chantecler, Del., Doninique, Holland, Java, Jersey Giant, Lamona, N.H., Plymouth Rock, R.I. Red, R.I. White, and Wyandotte breeds. The Asiatic Class includes the Brahma, Cochin, and Langshan breeds. The English Class includes the Australorp, Cornish, Dorking, Orpington, Redcap, and Sussex breeds. The Mediterranean Class includes the Ancona, Blue Andalusian, Catalanas, Leghorn, Minorca, Spanish, and Buttercup breeds. As would be appreciated by those of skill in the art, there are classes and breeds of poultry other than those listed above. The invention described herein is generally used on all classes and breeds of poultry.

Avian influenza viruses are diseases that pose significant threats to animal and human health and are a source of genetic diversity that permits the emergence of pandemic influenza. As used herein, avian influenza is influenza that adversely affects at least some poultry by causing flu symptoms, and possibly death, in the poultry. The fact that an influenza can be carried by some poultry without producing flu symptoms or adversely affecting the health of the poultry does not alter the fact that the influenza is an avian influenza and is a disease as long as the influenza adversely affects the health of at least some poultry. As used herein, a poultry that contracts avian influenza virus and that does not exhibit symptoms and/or that functions as a carrier of the virus is still said to have contracted the avian influenza disease. A poultry contracts avian influenza virus when the virus is in the body of the poultry.

As used herein, a disease is prevented before or after poultry is exposed to the disease, if (1) a medicament composition is administered to an animal internally (by ingestion, inhalation, injection, etc.), topically (on the skin for absorption into the body), or otherwise, and (2) the medicament composition prevents the poultry from contracting the disease and experiencing symptoms normally associated with the disease, or, if the poultry contracts the disease and experiences or doesn't experience in varying degrees of severity some or all of the symptoms normally associated with the disease, the poultry recovers from the disease to a normal healthy state.

As used herein, a disease is treated if a medicament composition is administered to poultry after the poultry has contracted a disease. As noted above, a poultry that contracts a disease may or may not exhibit symptoms associated with the disease.

The symptoms produced in poultry by avian influenza range from a mild illness to a highly contagious and rapidly fatal "highly pathogenic" form of the disease that can produce severe epidemics. Highly pathogenic avian influenza is characterized by sudden onset, severe and rapid death, and a mortality that can approach 100%.

Fifteen subtypes of influenza virus are known. All outbreaks of the highly pathogenic form that have occurred to date were caused by influenza A viruses of subtypes H5 and H7.

One problem with avian influenza viruses is that viruses of low pathogenicity can, after circulating for a relatively short period of time, mutate in highly pathogenic viruses.

Another problem with avian influenza viruses is that they are highly contagious.

A further problem with avian influenza viruses is that they are readily transmitted from farm to farm by mechanical means including, for example, contaminated equipment, vehicles, feed, cages, and clothing.

Still another problem with avian influenza is that highly pathogenic viruses can survive for long periods in the environment, especially when temperatures are low.

Still a further problem with avian influenza is that influenza A viruses, including subtypes from different species (i.e., humans and poultry), can swap or "reassort" genetic materials and merge. This reassortment process is known as antigenic "shift". Antigenic shift produce a novel subtype different from both parent viruses. Antigenic shift typically results in highly lethal pandemics. Since pigs are susceptible to infection with avian and mammalian viruses, including human strains, pigs can function as a "mixing vessel" for the scrambling of genetic material from human and avian viruses, resulting in the mergence of a novel subtype. Consequently, humans living in close proximity to domestic poultry and pigs have been thought to produce conditions favorable from the emergence of antigenic shift. Recent evidence, however, also suggests that humans themselves can serve as the "mixing vessel".

There are various routes of transmission of avian influenza. Consequently, a chicken at a first farm can possibly pass avian influenza virus to a pig or farmer at a farm. The farmer can contaminate his clothes and his tractor with the virus. The pig can pass the virus to the farmer, possibly after the pig has served as the "mixing vessel" described above. The avian influenza virus can then be transmitted to a chicken at a second farm via the clothes of the farmer (if the farmer visits farm), via pig (if the pig is sold to farm), and via tractor (if tractor is parked at farm or is used by a farmer inhabiting farm).

Direct avian-to-human influenza transmission was unknown before 1997 when the H5N1 virus jumped from chickens to humans in Hong Kong. Eighteen people were hospitalized, six died and three million chickens were slaughtered to contain the virus.

In 2003, highly pathogenic strains of avian influenza virus, including the H5N1 and H7N7 subtypes, again crossed from birds to humans and caused fatal disease. The year 2004 saw the largest outbreak of H5N1 avian flu in history prompting world governments and health authorities to call for emergency preparedness measures. This outbreak was an economic disaster for the poultry industry, caused loss of human life, and sounded alarm bells of an impending human influenza pandemic. With a human mortality rate of greater than 75%, it has been estimated that a human pandemic involving H5N1 could result in 100 million human deaths worldwide.

A critical step in avoiding a human influenza pandemic involving avian influenza is to reduce the incidence of human exposure to the virus. This can in large part be accomplished by controlling the infections in poultry. However, attempts at poultry vaccination programs for avian influenza have not been successful and there are currently no anti-avian influenza medications available for use by the poultry industry. Accordingly, it would be highly desirable to provide a method and composition for preventing and treating avian influenza in poultry.

SUMMARY OF THE PRESENT INVENTION

It is a principal object of the invention to provide a method and composition for preventing and treating avian influenza in poultry.

These and other objectives, features, and advantages of the present invention will become apparent from the following detailed description and the appended claims.

DETAILED DESCRIPTION OF THE PREFERRED EMBODIMENT

The present invention provides a composition and method for treating and preventing avian influenza in poultry.

The method comprises administering a treatment composition including a carrier and an anti-avian influenza ingredient comprising an appropriate combination of theaflavin, theaflavin-3,3'-digal (TF-3), theaflavin-3-monogallate (TF-2), theaflavin-3 gallate, theaflavin-3'-gallate, thearubigin, gallic acid and tannic acid (−)-epigallocatechin gallate (EGCG), (−)epigallocatechin (EGC), (−)epicatechin gallate (ECG), (+)-epicatechin (EC), (−)-gallocatechin gallate (GCG), and catechin.

The presently preferred theaflavins or derivatives are found in black tea and include, theaflavin (TF1), theaflavin-3 gallate (TF2a), theaflavin-3'-gallate (TF2b), theaflavin-3,3'-digallate (TF-3), thearubigin, gallic acid and tannic acid. We have demonstrated that theaflavin (TF1), theaflavin-3 gallate (TF2a), theaflavin-3'-gallate (TF2b), and theaflavin-3,3'-digallate (TF-3), inhibits H5N1 infections in mammalian cells by blocking the attachment and entry into the cells. Our data indicates that the higher the number of gallate groups on the theaflavin backbone, the higher the potency against the virus.

The presently preferred catechins are found in green tea or green tea extract (GTE) and include (−)-epigallocatechin gallate (EGCG), (−)epigallocatechin (EGC), (−) epicatechin gallate (ECG), (+)-epicatechin (EC), (−)-gallocatechin gallate (GCG), and catechin. We have demonstrated that (−)-epigallocatechin gallate (EGCG) in particular inhibits H5N1 infections in mammalian cells by blocking the attachment and entry into the cells.

If desired, the theaflavin (TF1), theaflavin-3 gallate (TF2a), theaflavin-3'-gallate (TF2b), theaflavin-3,3'-digal (TF-3), thearubigin, gallic acid, tannic acid, (−)epigallocatechin gallate (EGCG), (−)epigallocatechin (EGC), (−)epicatechin gallate (ECG), (+)-epicatechin (EC), (−)-gallocatechin gallate (GCG), or catechin molecules can be modified by attaching different molecules, by removing a portion(s) of the molecules, or by removing a portion(s) of the molecules and incorporating a different structure for the removed portion of the molecules.

The carrier can be a liquid or solid or combination thereof. The treatment composition can be administered directly to poultry by ingestion or inhalation or injection or topical application, can be admixed with solid foods or liquids fed to poultry, or can be admixed with compositions that are injected in or otherwise administered to poultry. The concentration in the treatment composition of the anti-avian influenza ingredient can be in the range of 0.1% by weight to 99.9% by weight, preferably 0.5% by weight to 50% by weight, most preferably 2.0% by weight to 25% by weight. The concentration of the anti-avian influenza ingredient in the feed or composition administered by ingestion or inhalation to the poultry is in the range of 0.001% to 99.9% by weight, preferably 0.005 to 40% by weight, most preferably 0.01 to 25% by weight. The amount of the active anti-avian influenza ingredient (i.e., an appropriate combination of theaflavin and theaflavin fractions) administered to poultry by ingestion, inhalation, or injection (preferably, although not necessarily, daily) is in the range of 0.1 mg to 2000 mg daily, preferably 0.5 mg to 500 mg daily, most preferably 1 mg to 200 mg daily. If the active anti-avian influenza ingredient is administered by injection into the tissue or blood stream of a chicken or other poultry, the dosage can vary as desired, but typically is in the range of 0.1 mg to 2000 mg daily, preferably 0.5 mg to 500 mg daily, most preferably 1 mg to 200 mg daily. The treatment composition can be administered any desired number of times with any desired intervals between treatments.

The quantity of the molecules administered to poultry can vary as desired. A treatment program for poultry can comprise a single treatment or can comprise a plurality of treatments.

Importantly, dosages including particular optimal ratios or combinations of the molecules are presently preferred.

The molecules are administered in a desired carrier. The molecules are soluble in both water and alcohol at room temperature. Consequently, administering the molecules in a liquid composition comprising water and/or alcohol as a carrier is readily achieved. However, molecules, when ingested, can be administered in a liquid or solid earner.

Accordingly, the formulas for Vira 38 products are as follows:

| Vira 38 One done is 10 ml | | |
|---|---|---|
| Elderberry | 4.0 g | 40% |
| *Echinacea* | 1.0 g | 10% |
| Epigallocatechin gallate (EGCG) | 1.0 g | 10% |
| Theaflavine (TF) | 1.0 g | 10% |
| N-Acetyl-L-Cysteine (NAC) | 1.0 g | 10% |
| Alpha Lipoic Acid (ALA) | 1.0 g | 10% |

| FluStat Per 10 ml | |
|---|---|
| EGCG | 2.0 g |
| TF | 1.0 g |
| NAC | 1.0 g |
| ALA | 1.0 g |

Example 1

A medicament composition containing 98.0% by weight of a supplemental chicken feed (as a carrier) and containing 2.0% by weight of an anti-avian influenza component consisting of polyphenolic fractions is prepared by admixing the supplemental chicken feed and polyphenolic fractions at room temperature. The polyphenolic fractions are in powder form. The supplemental chicken feed consists of selected conventional chicken feed components, including a majority by weight of dried sea weed meal, along with flax seed meal and dehydrated lemon powder. Any desired supplemental chicken feed can be utilized. It is recommended that one to two tablespoons (about 15 to 30 grams) of the treatment composition be admixed with five to ten pounds of primary conventional chicken feed and that the resulting medicament composition-primary chicken feed mixture be fed to chickens daily such that each chicken consumes about one-quarter to one-half pound of the medicament composition-primary chicken feed mixture each day.

As noted above, the medicament composition can, if desired, be administered directly to poultry without admixing the medicament composition with other water or feed that is administered to the poultry. In this instance, the medicament composition can become the primary chicken feed mixture, in which case the concentration of the anti-avian influenza active ingredient in the medicament composition can, if desired, be reduced (or increased).

Example 2

A medicament composition containing 98.0% by weight of the supplemental chicken feed (as a carrier) and containing 2.0% by weight of an anti-avian influenza component consisting of theaflavin-3,3'-digallate and an appropriate amount of at least one other polyphenolic fraction is prepared by admixing the chicken feed and the polyphenolic fractions at room temperature.

Example 3

A medicament composition containing 98.0% by weight of the supplemental chicken feed (as a carrier) and containing 2.0% by weight of an anti-avian influenza component consisting of theaflavin-3-monogallate and an appropriate amount of at least one other polyphenolic fraction is prepared by admixing the chicken feed and the polyphenolic fractions at room temperature.

Example 4

A medicament composition containing 98.0% by weight of the supplemental chicken feed (as a carrier) and containing 2.0% by weight of an anti-avian influenza component consisting of theraflavin-3 gallate and an appropriate amount of at least one other polyphenolic fraction is prepared by admixing the chicken feed and the polyphenolic fractions at room temperature.

Example 5

A medicament composition containing 98.0% by weight of the supplemental chicken feed (as a carrier) and containing 2.0% by weight of an anti-avian influenza component consisting of theaflavin-3'-gallate and an appropriate amount of at least one other polyphenolic fraction is prepared by admixing the chicken feed and the polyphenolic fractions at room temperature.

Example 6

A medicament composition containing 98.0% by weight of the supplemental chicken feed (as a carrier) and containing 2.0% by weight of an anti-avian influenza component thearubigin and an appropriate amount of at least one other polyphenolic fraction is prepared by admixing the chicken feed and the polyphenolic fractions at room temperature.

Example 7

A medicament composition containing 98.0% by weight of the supplemental chicken feed (as a carrier) and containing 2.0% by weight of an anti-avian influenza component gallic acid and an appropriate amount of at least one other polyphenolic fraction is prepared by admixing the chicken feed and the polyphenolic fractions at room temperature.

Example 8

A medicament composition containing 98.0% by weight of the supplemental chicken feed (as a carrier) and containing 2.0% by weight of an anti-avian influenza component consisting of tannic acid and an appropriate amount of at least one other polyphenolic fraction is prepared by admixing the chicken feed and the polyphenolic fractions at room temperature.

Example 9

A medicament composition containing 98.0% by weight of the supplemental chicken feed (as a carrier) and containing 2.0% by weight of an anti-avian influenza component consisting of (−)-epigallocatechin gallate (EGCG) and an appropriate amount of at least one other polyphenolic fraction is prepared by admixing the chicken feed and the polyphenolic fractions at room temperature.

Example 10

A medicament composition containing 98.0% by weight of the supplemental chicken feed (as a carrier) and containing 2.0% by weight of an anti-avian influenza component consisting of (−)epigallocatechin (EGC) and an appropriate amount of at least one other polyphenolic fraction is prepared by admixing the chicken feed and the polyphenolic fractions at room temperature.

Example 11

A medicament composition containing 98.0% by weight of the supplemental chicken feed (as a carrier) and containing 2.0% by weight of an anti-avian influenza component consisting of (−)epicatechin gallate (ECG) and an appropriate amount of at least one other polyphenolic fraction is prepared by admixing the chicken feed and the polyphenolic fractions at room temperature.

Example 12

A medicament composition containing 98.0% by weight of the supplemental chicken feed (as a carrier) and containing 2.0% by weight of an anti-avian influenza component consisting of (+)-epicatechin (EC) and an appropriate amount of at least one other polyphenolic fraction is prepared by admixing the chicken feed and the polyphenolic fractions at room temperature.

Example 13

A medicament composition containing 98.0% by weight of the supplemental chicken feed (as a carrier) and containing 2.0% by weight of an anti-avian influenza component consisting of (−)-gallocatechin gallate (GCG) and an appropriate amount of at least one other polyphenolic fraction is prepared by admixing the chicken feed and the polyphenolic fractions at room temperature.

Example 14

A medicament composition containing 98.0% by weight of the supplemental chicken feed (as a carrier) and containing 2.0% by weight of an anti-avian influenza component consisting of catechin and an appropriate amount of at least one other polyphenolic fraction is prepared by admixing the chicken feed and the polyphenolic fractions at room temperature.

Example 15

Example 1 is repeated, except water is utilized as a carrier in place of the supplemental chicken feed.

Example 16

Example 2 is repeated, except water is utilized as a carrier in place of the supplemental chicken feed.

Example 17

Example 3 is repeated, except water is utilized as a carrier in place of the supplemental chicken feed.

Example 18

Example 4 is repeated, except water is utilized as a carrier in place of the supplemental chicken feed.

Example 19

Example 5 is repeated, except water is utilized as a carrier in place of the supplemental chicken feed.

Example 20

Example 6 is repeated, except water is utilized as a carrier in place of the supplemental chicken feed.

Example 21

Example 7 is repeated, except water is utilized as a carrier in place of the supplemental chicken feed.

Example 22

Example 8 is repeated, except water is utilized as a carrier in place of the supplemental chicken feed.

Example 23

Example 9 is repeated, except water is utilized as a carrier in place of the supplemental chicken feed.

Example 24

Example 10 is repeated, except water is utilized as a carrier in place of the supplemental chicken feed.

Example 25

Example 11 is repeated, except water is utilized as a carrier in place of the supplemental chicken feed.

Example 26

Example 12 is repeated, except water is utilized as a carrier in place of the supplemental chicken feed.

Example 27

Example 13 is repeated, except water is utilized as a carrier in place of the supplemental chicken feed.

Example 28

Example 14 is repeated, except water is utilized as a carrier in place of the supplemental chicken feed.

Example 29

Examples 1 to 28 are repeated, except that the concentration of the anti-avian influenza component is 5% instead of 2.0%.

Example 30

Examples 1 to 28 are repeated, except that the concentration of the anti-avian influenza component is 10% instead of 2.0%.

Example 31

Examples 1 to 28 are repeated, except that the concentration of the anti-avian influenza component is 50% instead of 2.0%.

Example 32

Examples 1 to 28 are repeated, except that the concentration of the anti-avian influenza components is 90% instead of 2.0%.

Example 33

Each ten pounds of primary conventional chicken feed is admixed with two tablespoons (about 30 grams) of the medicament composition of Example 1 to produce a resulting medicament composition-primary chicken feed mixture. One hundred healthy adult chickens are selected and are exposed to and directly contacted with an avian influenza virus such that it is highly likely each individual will develop avian influenza disease. Fifty of the chickens comprise a test group. Each day for a period of ten (10) days prior to said exposure, each chicken in the test group is fed one-tenth to one-half pound of the medicament composition-primary chicken feed mixture. The remaining fifty (50) chickens comprise a control group. Each day for a period of ten (10) days prior to said exposure, each chicken in the control group is fed primary chicken feed mixture that does not include any of the medicament composition of Example 1. During the next ten days following exposure to the avian influenza virus, forty chickens in the control group develop avian influenza. None of the chickens in the test group contract avian influenza.

Example 34

Example 33 is repeated except that each ten pounds of primary conventional chicken feed is admixed with two tablespoons (about 30 grams) of the medicament composition of Example 2 to produce the resulting medicament composition-primary chicken feed mixture that is administered to the test group. Similar results are obtained.

Example 35

Example 33 is repeated except that each ten pounds of primary conventional chicken feed is admixed with two tablespoons (about 30 grams) of the medicament composition of Example 3 to produce the resulting medicament composition-primary chicken feed mixture that is administered to the test group. Similar results are obtained.

Example 36

Example 33 is repeated except that each ten pounds of primary conventional chicken feed is admixed with two tablespoons (about 30 grams) of the medicament composition of Example 4 to produce the resulting medicament composition-primary chicken feed mixture that is administered to the test group. Similar results are obtained.

Example 37

Example 33 is repeated except that each ten pounds of primary conventional chicken feed is admixed with two tablespoons (about 30 grams) of the medicament composition of Example 5 to produce the resulting medicament composition-primary chicken feed mixture that is administered to the test group. Similar results are obtained.

Example 38

Example 33 is repeated except that each ten pounds of primary conventional chicken feed is admixed with two tablespoons (about 30 grams) of the medicament composition of Example 6 to produce the resulting medicament composition-primary chicken feed mixture that is administered to the test group. Similar results are obtained.

Example 39

Example 33 is repeated except that each ten pounds of primary conventional chicken feed is admixed with two tablespoons of the aqueous medicament composition of Example 7 to produce the resulting medicament composition-primary chicken feed mixture that is administered to the test group. Similar results are obtained. As would be appreciated by those of skill in the art, the aqueous medicament composition of Example 7 (or any other aqueous treatment composition) can be added to the water that the chickens or other poultry drink instead of or in addition to adding the aqueous treatment composition to the primary chicken feed.

Example 40

Example 33 is repeated except that each ten pounds of primary conventional chicken feed is admixed with two tablespoons of the aqueous medicament composition of Example 8 to produce the resulting medicament composition-primary chicken feed mixture that is administered to the test group. Similar results are obtained.

Example 41

Example 33 is repeated except that each ten pounds of primary conventional chicken feed is admixed with two tablespoons of the aqueous medicament composition of Example 9 to produce the resulting medicament composition-primary chicken feed mixture that is administered to the test group. Similar results are obtained.

Example 42

Example 33 is repeated except that each ten pounds of primary conventional chicken feed is admixed with two tablespoons of the aqueous medicament composition of Example 10 to produce the resulting medicament composition-primary chicken feed mixture that is administered to the test group. Similar results are obtained.

Example 43

Example 33 is repeated except that each ten pounds of primary conventional chicken feed is admixed with two tablespoons of the aqueous medicament composition of Example 11 to produce the resulting medicament composition-primary chicken feed mixture that is administered to the test group. Similar results are obtained.

Example 44

Example 33 is repeated except that each ten pounds of primary conventional chicken feed is admixed with two tablespoons of the aqueous medicament composition of Example 12 to produce the resulting medicament composition-primary chicken feed mixture that is administered to the test group. Similar results are obtained.

Example 45

Example 33 is repeated except that each ten pounds of primary conventional chicken feed is admixed with two tablespoons of the aqueous medicament composition of Example 13 to produce the resulting medicament composition-primary chicken feed mixture that is administered to the test group. Similar results are obtained.

Example 46

Example 33 is repeated except that each ten pounds of primary conventional chicken feed is admixed with two tablespoons of the aqueous medicament composition of Example 14 to produce the resulting medicament composition-primary chicken feed mixture that is administered to the test group. Similar results are obtained.

Example 47

Examples 33 to 46 are repeated except that in each example the medicament composition utilized to administer polyphenolic fractions to each member of the test group includes 95% by weight of supplemental chicken feed or water, as the case may be, and 5% by weight of the polyphenolic fractions. Similar results are obtained.

Example 48

Example 33 to 46 are repeated except that in each example the medicament composition utilized to administer polyphenolic fractions to each member of the test group includes 50% by weight of supplemental chicken feed or water, as the case may be, and 50% by weight of the polyphenolic fractions. Similar results are obtained.

Example 49

Examples 33 to 48 are repeated except that in each example the amount of the medicament composition-primary chicken feed mixture ingested each day by each member in the test group includes only 0.1 gram of the particular theaflavin fractions or thearubigin recited in the example. Similar results are obtained.

Example 50

Examples 33 to 48 are repeated except that in each example the amount of the medicament composition-primary chicken feed mixture ingested each day by each member in the test group includes 5 grams of the particular theaflavin fractions or thearubigin recited in the example. Similar results are obtained.

Example 51

Examples 33 to 50 are repeated except that in Example 17 one hundred turkeys, and not one hundred chickens, are provided. Similar results are obtained in each Example 33 to 50 when the turkeys, and not the chickens, are utilized.

Example 52

Examples 33 to 50 are repeated except that in Example 33 one hundred ducks, and not one hundred chickens, are provided. Similar results are obtained in each Example 33 to 50 when the ducks, and not the chickens, are utilized.

Example 53

Examples 33 to 50 are repeated except that in Example 17 one hundred pheasants, and not one hundred chickens, are provided. Similar results are obtained in each Example 33 to 50 when the pheasants, and not the chickens, are utilized.

Example 54

Examples 33 to 50 are repeated except that in Example 17 one hundred geese, and not one hundred chickens, are provided. Similar results are obtained in each Example 33 to 50 when the geese, and not the chickens, are utilized.

One embodiment of the invention comprises an article of manufacture consisting of an influenza medicament composition including a concentration of one or more polyphenolics. The concentration of the polyphenolics in the feed or other composition administered by ingestion, by injection, topically or by inhalation to the poultry is in the range of 0.001% to 99.9% by weight, preferably 0.005 to 40% by weight, most preferably 0.01 to 25% by weight.

Another embodiment of the invention comprises a method for producing an influenza treatment composition, comprising the steps of processing tea leaves and other botanical sources to produce a concentrate including at least 5% by weight of polyphenolics.

Tea is one presently preferred source of the polyphenolics.

Green tea is freshly picked tea that typically has been processed to inactivate enzymes that are found in the tea and that oxidize chemical components found in the tea. One process used to inactivate enzymes is heat treatment. For example, during the production of green tea, tea leaves ordinarily are steamed, rolled and dried. Green tea includes (−)-epigallocatechin gallate (EGCG), (−)epigallocatechin (EGC), (−)epicatechin gallate (ECG), (+)-epicatechin (EC), (−)-gallocatechin gallate (GCG), and catechin. Therefore green tea includes catechins and epicatechins.

Black tea is produced by processing freshly picked tea leaves to alter chemical components in the tea leaves. Such processing includes fermentation that utilizes enzymes naturally present in the tea to oxidize chemical components in the tea leaves. Black tea typically is allowed to oxidize for two to four hours. Oolong tea falls somewhere between green and black teas, in that the leaves are only partially oxidized. Black tea is sometimes called fermented green tea, although this description ordinarily is not technically accurate. In one process for producing black tea, freshly picked leaves are placed in long troughs for withering. Cold air is blown through the troughs to concentrates cell sap and about twenty percent of the moisture is removed from the leaves. This withering process lasts for about a day. The leaves are then placed in equipment that crushes, tears and curls the leaves. This exposes sap in the leaves to air. The resulting tea leaf pieces are placed in a fermenting drum for oxidation. During oxidation the polyphenols theaflavin and theaflavin form and, if fermentation is prolonged a sufficient time, thearubigin is formed. Thearubigin gives a rich color to the tea. The theaflavin fractions include fractions, theaflavin-3-gallate, theaflavin-3'-gallate, and theaflavin-3,3'-digallate, which fractions are sometimes described as TF1, TF2, and TF 3. Theaflavin has been described as a doubly condensed catechin substance based on epigallocatechin-3-gallate (ECG). After forty-five minutes to one hour, the tea is put in a drying machine at about 50° C. to kill the enzymes and end fermentation. The tea is put in a dryer for about ten minutes to complete the process. Special processes are used to select and combine particular theaflavin fractions.

Green tea may also contain some theaflavins. It has been noted that seventy-five milligrams of theaflavins is equivalent to the quantity of theaflavins found in as much as thirty-five cups of green tea or seven cups of black tea.

A variety of methods are known for either extracting polyphenolics from tea to produce the polyphenolic fraction extracts that normally have a concentration of polyphenolics greater than that found in the tea, or for producing tea with increased polyphenolic fraction concentrations.

Compositions that enhance the effectiveness of the anti-avian influenza ingredient(s) described herein can be combined with the anti-avian influenza ingredient(s). Alternatively, the anti-avian influenza ingredient(s) can be combined with other drugs or compositions to enhance the effectiveness of such other drugs.

One skilled in the art will understand that the embodiment of the present invention described above is exemplary only and not intended to be limiting.

It will thus be seen that the objects of the present invention have been fully and effectively accomplished. The above embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A method for treating and reducing the risk of avian influenza in a poultry, comprising a step of administering to said poultry an effective amount of a composition comprising an anti-avian influenza ingredient containing a polyphenolic selected from the group consisting of theaflavin, theaflavin-3,3'-digallate, theaflavin-3-monogallate, theaflavin-3 gallate, theaflavin-3'-gallate, thearubigin, gallic acid, tannic acid, (−)-epigallocatechin gallate (EGCG), (−)epigallocatechin (EGC), (+)-epicatechin (EC), (−)-gallocatechin gallate (GCG), catechin, and combinations thereof, wherein the composition is administered directly to poultry by inhalation.

2. The method of claim 1, wherein the composition comprises the anti-avian influenza ingredient in combination with a carrier.

3. The method of claim 2, wherein the composition comprises 98.0% by weight of the carrier and 2.0% by weight of the anti-avian influenza ingredient.

4. The method of claim 1, wherein the polyphenolic is extracted from tea leaves.

5. The method of claim 3, wherein the polyphenolic is extracted from tea leaves.

6. The method of claim 1, wherein theaflavin, theaflavin-3,3'-digallate, theaflavin-3 gallate, thearubigin, gallic acid, and tannic acid are extracted from black tea.

7. The method of claim 3, wherein theaflavin, theaflavin-3,3'-digallate, theaflavin-3 gallate, thearubigin, gallic acid, and tannic acid are extracted from black tea.

8. The method of claim 1, wherein (−)-epigallocatechin gallate (EGCG), (−)epigallocatechin (EGC), (−)epicatechin gallate (ECG), (+)-epicatechin (EC), (−)gallocatechin gallate (GCG), and catechin are extracted from green tea.

9. The method of claim 3, wherein (−)-epigallocatechin gallate (EGCG), (−)epigallocatechin (EGC), (−)epicatechin gallate (ECG), (+)-epicatechin (EC), (−)gallocatechin gallate (GCG), and catechin are extracted from green tea.

10. A method for treating and reducing the risk of avian influenza in a poultry, comprising a step of administering to said poultry an effective amount of a composition comprising an anti-avian influenza ingredient containing a polyphenolic selected from the group consisting of theaflavin, theaflavin-3,3'-digallate, theaflavin-3-monogallate, theaflavin-3 gallate, theaflavin-3'-gallate, thearubigin, gallic acid, tannic acid, (−)-epigallocatechin gallate (EGCG), (−)epigallocatechin (EGC), (+)-epicatechin (EC), (−)-gallocatechin gallate (GCG), catechin, and combinations thereof, wherein the composition is administered directly to poultry by injection.

11. The method of claim n, wherein the composition comprises the anti-avian influenza ingredient in combination with a carrier.

12. The method of claim 11, wherein the composition comprises 98.0% by weight of the carrier and 2.0% by weight of the anti-avian influenza ingredient.

13. The method of claim 10, wherein the polyphenolic is extracted from tea leaves.

14. The method of claim 12, wherein the polyphenolic is extracted from tea leaves.

15. The method of claim 10, wherein theaflavin, theaflavin-3,3'-digallate, theaflavin-3 gallate, thearubigin, gallic acid, and tannic acid are extracted from black tea.

16. The method of claim 12, wherein theaflavin, theaflavin-3,3'-digallate, theaflavin-3 gallate, thearubigin, gallic acid, and tannic acid are extracted from black tea.

17. The method of claim 10, wherein (−)-epigallocatechin gallate (EGCG), (−)epigallocatechin (EGC), (−)epicatechin gallate (ECG), (+)-epicatechin (EC), (−)gallocatechin gallate (GCG), and catechin are extracted from green tea.

18. The method of claim 12, wherein (−)-epigallocatechin gallate (EGCG), (−)epigallocatechin (EGC), (−)epicatechin gallate (ECG), (+)-epicatechin (EC), (−)gallocatechin gallate (GCG), and catechin are extracted from green tea.

* * * * *

UNITED STATES PATENT AND TRADEMARK OFFICE
CERTIFICATE OF CORRECTION

Page 1 of 1

PATENT NO.       : 8,916,211 B2
APPLICATION NO.  : 13/900235
DATED            : December 23, 2014
INVENTOR(S)      : Charles Hensley and Sung Pyo It is certified that error appears in the above-identified patent and that said Letters Patent is hereby corrected as shown below:

In the Claims:

Column 14, line 7: After "claim" delete "n," and replace with -- 10, --.

Signed and Sealed this
Seventh Day of April, 2015

Michelle K. Lee
*Director of the United States Patent and Trademark Office*